(12) United States Patent
Pevzner et al.

(10) Patent No.: US 7,520,666 B2
(45) Date of Patent: Apr. 21, 2009

(54) METHOD AND SYSTEM FOR DETECTING DAMAGE IN LAYERED STRUCTURES

(75) Inventors: Pavel Pevzner, Haifa (IL); Tanchum Weller, Haifa (IL); Avraham Berkovits, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 65 days.

(21) Appl. No.: 11/635,085

(22) Filed: Dec. 7, 2006

(65) Prior Publication Data

US 2007/0223557 A1    Sep. 27, 2007

Related U.S. Application Data

(60) Provisional application No. 60/742,684, filed on Dec. 7, 2005.

(51) Int. Cl.
*G01N 25/72* (2006.01)
*G01J 5/00* (2006.01)

(52) U.S. Cl. ............................ 374/5; 374/121; 374/131; 374/4; 374/57; 374/45

(58) Field of Classification Search ............... 374/4, 374/5, 121, 131, 45, 57
See application file for complete search history.

(56) References Cited

U.S. PATENT DOCUMENTS

| | | | | | |
|---|---|---|---|---|---|
| 5,086,220 | A | * | 2/1992 | Berthold et al. ............ | 250/227.2 |
| 5,260,766 | A | * | 11/1993 | Armitage .................. | 356/237.1 |
| 5,302,025 | A | * | 4/1994 | Kleinerman ................ | 374/131 |
| 5,306,088 | A | * | 4/1994 | Zoerner ..................... | 374/131 |
| 5,775,808 | A | * | 7/1998 | Pan .......................... | 374/161 |
| 5,821,861 | A | * | 10/1998 | Hartog et al. .............. | 340/584 |
| 5,822,222 | A | * | 10/1998 | Kaplinsky et al. .......... | 702/134 |
| 6,527,441 | B1 | * | 3/2003 | Cranch et al. .............. | 374/161 |
| 6,595,684 | B1 | * | 7/2003 | Casagrande et al. .......... | 374/5 |
| 2002/0050566 | A1 | * | 5/2002 | Nilsson et al. ............ | 250/341.6 |
| 2003/0219059 | A1 | * | 11/2003 | Scott ........................ | 374/5 |
| 2004/0114662 | A1 | * | 6/2004 | Messler ..................... | 374/130 |

* cited by examiner

*Primary Examiner*—Gail Verbitsky
*Assistant Examiner*—Mirellys Jagan
(74) *Attorney, Agent, or Firm*—Pearl Cohen Zedek Latzer, LLP

(57) ABSTRACT

A system and method for detecting structural damage in a layered structure, the method compromising: providing an array of optical fibers attached to the layered structure; providing a laser source for emitting light into the optical fibers; providing a thermal imaging device; transferring laser light beam through each of the optical fibers of the array; acquiring at least one thermal image of an external surface of the layered structure; and detecting existence of one or more hot spots on the external surface indicative of a location of damage in the layered structure.

18 Claims, 2 Drawing Sheets

METHOD AND SYSTEM FOR DETECTING DAMAGE IN LAYERED STRUCTURES

CROSS REFERENCE TO RELATED APPLICATIONS

This application claims the benefit of U.S. Provisional Patent Application No. 60/742,684, filed on Dec. 7, 2005, which is incorporated in its entirety herein by reference.

FIELD OF THE INVENTION

The present invention relates to a method and system for detecting structural damage and irregularities in layered structures, such as (but not limited to) composite materials. Optical fibers embedded between the surfaces of adjacent layers of composite materials or bonded on hidden internal surfaces deform and crack due to damage resulting from static and dynamic loading of the composite materials. The optical fibers are so arranged as to cover an area to be monitored for cracks and structural damages in the composite material. The detecting system is based on laser-light energy transmitted through the fibers and is converted into thermal energy at the location of cracks in the fibers. The thermal energy is expressed as a rise in the local temperature in the vicinity of the cracks, thus providing for a method for the detection and location of structural damage in the composite material by the use of an infrared camera.

BACKGROUND OF THE INVENTION

Techniques which use embedded optical fibers in composite structures are considered to be very promising for nondestructive detection of damage. In addition to measuring response of composite structures to external stimuli, embedded fiber optic sensors would make ideal "nerves" for sensing the local integrity of such structures. Their optical properties and their compatibility with the properties of composite materials (extremely light weight, small diameter, resistance to corrosion and fatigue, mechanical properties similar to those of composites and insensitivity to ambient magnetic fields) have been exploited in many studies as described and discussed by T. Valis in his publication: Localized and distributed fiber-optic sensors embedded in composite materials, University of Toronto Institute for Aerospace Studies (UTIAS) report 346, September 1992. CN ISSN 0082-5255.

In many cases fiber optic strain sensors have already replaced conventional electrical sensors to measure the excited frequencies and amplitudes in a structure, that were formerly measured with the aid of accelerometers or strain gauges.

Examples of such strain measurements are given by: L. J. Buckley and G. C. Neumeister, Fiber optic strain measurements using an optically-active polymer, Smart Materials Structures, 1(1):1-4, March 1992. Additional examples are given in an article by P. J. Masalkar et al. in pages 230-235 of volume 2443 of the publication of the International Society for Optical Engineering (SPIE): Smart Structures and Integrated Systems 1995, Smart Structures and Materials under the title: Use of optical fiber strain sensor for damage detection in composite structures, published in San Diego, Calif. in February-March 1995. In the same publications in pages 308-312, J. P. Andrews and E. J. Zisk, published an article: Use of optical fiber strain sensor for damage detection in composite structures.

In numerous studies optic fibers have been applied for "health" monitoring systems in composite materials. An example of such use is given by R. M. Measures in a summary of the May 1990 meeting of the Canadian Aeronautics and Space Institute: Progress in the development of fiber-optic smart structures. An additional example is given in an article by D. W. Glossop et al. in the journal Composites, 21(1):71-80, January 1990: Optical fibre damage detection for an aircraft composite leading edge.

Methods for using optic fibers for damage detection include:

1) Use of optic fibers as integral strain sensors and or integral sensors for vibration measurements, either intensity-based or, more commonly, interferometry-based. The latter includes the Bragg, Mach-Zender, Michelson, Fabry-Perot and Sagnac interferometers and high birefrigence polarisation-mode interferometer.

2) Methods employing the fracture of the optic fiber sensor are based on the fact that preliminarily weakened fibers, embedded in a composite structure, crack at points where damage occurs in the structure. These methods use various techniques to determine the location of the crack in the fiber, such as segments of optic fibers connected by Bragg gratings, optical fibers disposed orthogonally, measurements of back reflection and backscattering from the crack. Using preliminarily weakened optic fibers embedded in a composite structure, Measures and Glossop identified cracks in the areas at which damage occurred in the structure, by locating cracks in the optic fibers by light leakage from these cracks through translucent composite material. They successfully located both impact and quasi-statically induced damage, and could map the growth of a region of damage with increasing load.

In contrast to the light emission methods, the approach of the system and method of the present invention identifies cracks in optic fibers by the rise in temperature in the neighborhood of a crack caused by the partial transformation of the light passing through optical fibers to thermal energy.

SUMMARY OF THE INVENTION

There is thus provided, in accordance with some preferred embodiments of the present invention, a method for detecting structural damage in a layered structure, the method comprising:

providing an array of optical fibers attached to the layered structure;

providing a laser source for emitting light into the optical fibers;

providing a thermal imaging device;

transferring laser light beam through each of the optical fibers of the array;

acquiring at least one thermal image of an external surface of the layered structure;

detecting existence of one or more hot spots oil the external surface indicative of a location of damage in the layered structure.

Furthermore, in accordance with some preferred embodiments of the present invention, the thermal imaging device comprises an IR camera.

Furthermore, in accordance with some preferred embodiments of the present invention, the laser source is connected to the array of optical fibers through a splicer.

Furthermore, in accordance with some preferred embodiments of the present invention, the method comprises acquiring a sequence in time of thermal images of the external surface of the layered structure in order to detect dynamically thermal changes on the surface indicative of a location of damage in the layered structure and damage progress in time.

Furthermore, in accordance with some preferred embodiments of the present invention, the method comprises embedding the array of optical fibers in the layered structure.

Furthermore, in accordance with some preferred embodiments of the present invention, the method comprises bonding the array of optical fibers to an internal surface of the layered structure.

Furthermore, in accordance with some preferred embodiments of the present invention, the layered structure is made of composite material.

Furthermore, in accordance with some preferred embodiments of the present invention, the layered structure comprises a laminate.

Furthermore, in accordance with some preferred embodiments of the present invention, the array of optical fibers comprises an array of substantially parallel optical fibers.

Furthermore, in accordance with some preferred embodiments of the present invention, the array of optical fibers comprises a grid of optical fibers.

Furthermore, in accordance with some preferred embodiments of the present invention, there is provided a system for detecting structural damage in a layered structure, the system compromising:

an array of optical fibers attached to the layered structure;

a laser source for emitting a laser light beam into the optical fibers;

a thermal imaging device for acquiring one or more images of an external surface of the layered structure for detecting existence of one or more hot spots on the external surface indicative of a location of damage in the layered structure.

Furthermore, in accordance with some preferred embodiments of the present invention, the system further provided with a processing unit for receiving image data from the thermal imaging device and processing the image data to detect existence and location of damage in the layered structure.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF PREFERRED EMBODIMENTS

The present invention relates to a system and method for detecting local structural damage and irregularities in structures made of layers (laminate structures) by the use of optical fibers embedded in the layers or and externally tightly bounded to the laminate.

The system and method of structural damage detection of the present invention is based on the physical phenomena that part of the light energy emitted by a laser beam transforms to thermal energy at locations of cracks in passing through optic fibers.

The term "light" refers to all forms of laser emitted radiation that is transformed to thermal energy upon encountering a crack in an optical fiber.

In a preferable embodiment the system and method relates to detecting local structural damage and irregularities in structures of composite material.

Experimental results in the Aerospace Structures Laboratory, Technion Israel Institute of Technology (Haifa, Israel) have demonstrated the feasibility of detecting and monitoring the "hot spots" on the composite plate surface caused by detecting heat emission from the optic fiber cracking with an infrared camera. The influence of parameters such as depth of the fiber below the surface of the plate, heat conductivity coefficient and light power, on the temperature rise and distribution were determined so as to be able to pinpoint the location of the damage in the optical fibers and thus in the composite material plate.

In accordance to the present invention, the use of an infrared camera, as previously explained, enables the acquisition of a "thermal signature" of a surface of a given structure; the "thermal signature" meaning a temperature-mapping of the surface at any given moment. If and when structural damage is sustained by material composing the structure, the cracked embedded or tightly bound optical fibers emit heat that changes the thermal signature of the surface of the structure. By comparing the thermal signature image of a surface from different times the detection and location of sustained damage can be monitored. The monitoring of the thermal signature can be carried out continuously and thus can (also) serve as a tool for a dynamic observation and detection of sustained structural damages.

The use of embedded and or tightly bound optical fibers for obtaining changes in the thermal signature of a surface of structure in the event of damage enables the use of the system and method of the present invention for monitoring for structural damages in crucial "hidden" surfaces such as the inner walls of fuel tanks or the inner structures of airplane wings, where monitoring on a regular basis is difficult and expensive.

Given below is a clarification of an example of a preferred embodiment of the detection system and method as implied in the monitoring of damage sustained by a plate of composite material.

Figure 1:
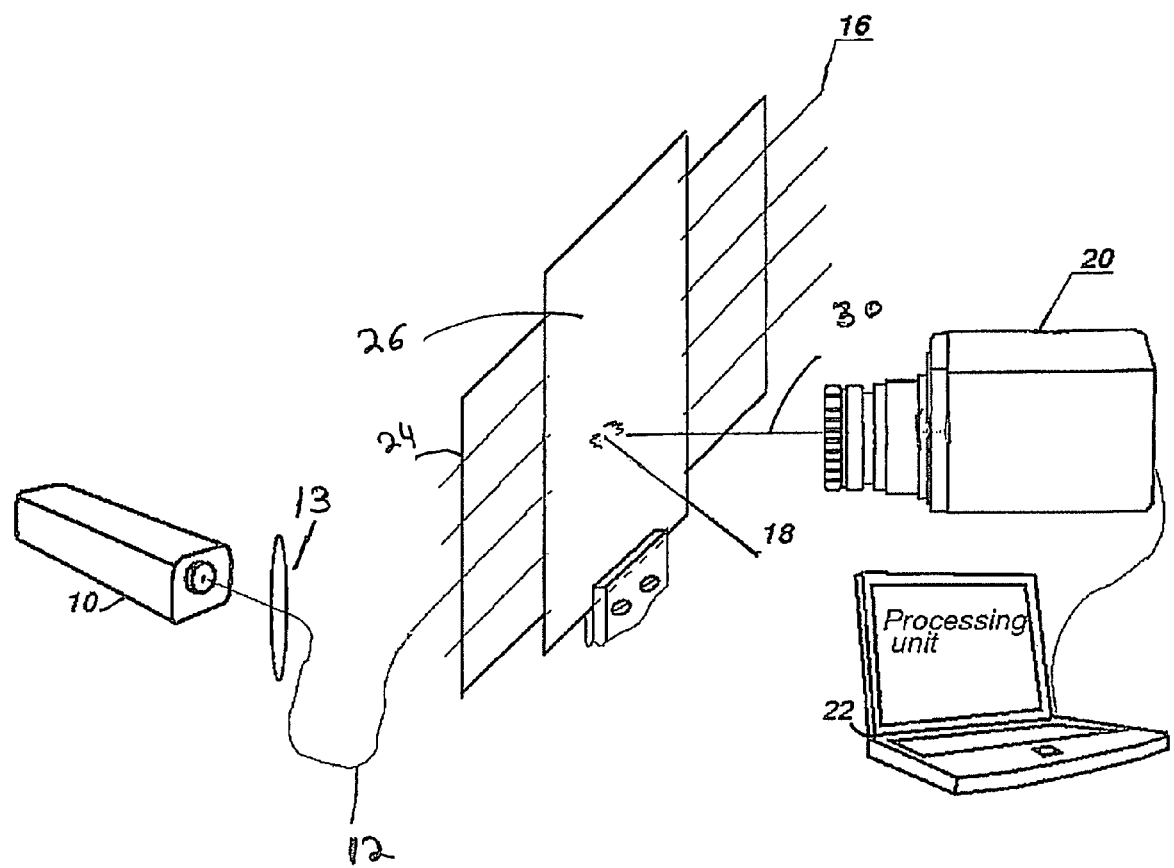
FIG. 1 is a schematic illustration of a system for detection of damage in composite material utilizing embedded optical fibers, a laser and an infrared camera, in accordance with the method of the present invention.

FIG. 1 illustrates a system for detection of damage in composite material in accordance to the method of the present invention. The method comprises a laser (10), that emits a light beam into a connection optical fiber (12). The light passes from the connection fiber to an optic fiber splicer (24), that distributes it to an array of optical fibers (16), that run through the composite material plate (26) being examined for structural damage.

The embedded fibers in the plate of the composite material are structured and placed so that structural damage caused to the plate will simultaneously cause cracks in the fibers. On encountering a crack in an optical fiber the transmitted light partially transforms to heat energy at the location of the crack (18). The heat is emitted to the surface of the plate, raises the local temperature, and is detected by an infrared camera (20), indicated by the vision path of the camera as (30).

In a preferable embodiment of the present invention, the method for detection of structural damage in a composite material also includes in the measurement system an optical system, designated as (13) in FIG. 1.

In yet another preferable embodiment of the present invention, the method for detection of structural damage in composite material also includes in the measurement system a processing unit, designated as (22) in FIG. 1, that analyses the data from the infrared camera (20).

Figure 2:
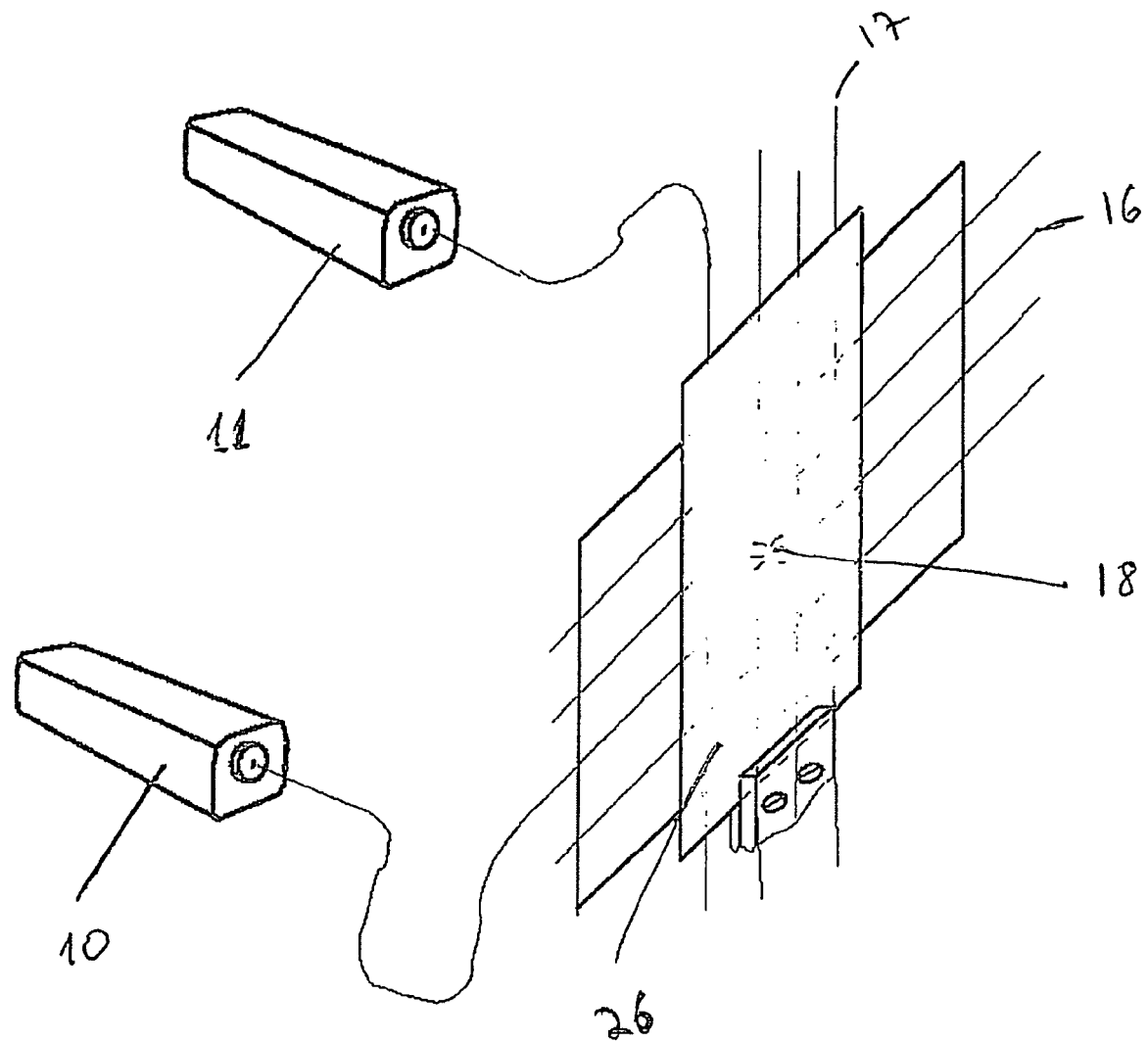
FIG. 2 is a schematic illustration of two unites of the detection system illustrated in FIG. 1 operating simultaneously for the exact determination of the location of the damage in the plate of composite material.

FIG. 2 is a schematic illustration of two unites of the detection system illustrated in FIG. 1 operating simultaneously for the exact determination of the location of the damage in the plate of composite material. Two lasers (10 and 11) emit light into a grid of optical fibers, designated by fibers running the length (16) and breath (17) of the plate of composite material (26). By the detection of the heat emission caused by the deformation or cracks in optical fibers in the length and breath dimensions the exact location of the structural damage (18) in the plate of the composite material can be pinpointed.

The method of the present invention is fairly accurate and reliable in locating damage, simple and easy to imply and can make use of optic fibers which have already been embedded into a structure for other purposes, such as strain, temperature and frequency measurements. The method can also work simultaneously with other methods, such as backscattering from the crack, to exact pinpoint a remote location where the crack in a fiber has occurred.

It should be clear that the description of the embodiments and attached Figures set forth in this specification serves only for a better understanding of the invention, without limiting its scope.

It should also be clear that a person skilled in the art, after reading the present specification could make adjustments or amendments to the attached Figures and above described embodiments that would still be covered by the present invention.

The invention claimed is:

1. A method for detecting structural damages in a layered structure, the method comprising:
   providing an array of optical fibers attached to the layered structure;
   providing a laser source for emitting light into the optical fibers;
   providing a thermal imaging device;
   transferring laser light beam through each of the optical fibers of the array;
   acquiring using the thermal imaging device at least one thermal image of an external surface of the layered structure; and
   detecting existence of one or more hot spots on the external surface indicative of a location of damage in the layered structure.

2. The method of claim 1, wherein the thermal imaging device comprises an IR camera.

3. The method of claim 1, wherein the laser source is connected to the array of optical fibers through a splicer.

4. The method of claim 1, wherein the step of acquiring using the thermal imaging device at least one thermal image of an external surface of the layered structure comprises acquiring a sequence in time of thermal images of the external surface of the layered structure in order to detect dynamic thermal changes on the surface indicative of a location of damage in the layered structure and damage progress in time.

5. The method of claim 1, comprising embedding the array of optical fibers in the layered structure.

6. The method of claim 1, comprising bonding the array of optical fibers to an internal surface of the layered structure.

7. The method of claim 1, wherein the layered structure is made of composite material.

8. The method of claim 1, wherein the layered structure comprises a laminate.

9. The method of claim 1, wherein the array of optical fibers comprises an array of substantially parallel optical fibers.

10. The method of claim 1, wherein the array of optical fibers comprises a grid of optical fibers.

11. A system for detecting structural damage in a layered structure, the system comprising:
    an array of optical fibers attached to the layered structure;
    a laser source for emitting a laser light beam into the optical fibers;
    a thermal imaging device for acquiring one or more images of an external surface of the layered structure for detecting existence of one or more hot spots on the external surface indicative of a location of damage in the layered structure.

12. The system of claim 11, further provided with a processing unit for receiving image data from the thermal imaging device and processing the image data to detect existence and location of damage in the layered structure.

13. The system of claim 11, wherein the thermal imaging device comprises an IR camera.

14. The system of claim 11, provided with a splicer for distributing light from the laser beam into the array of optical fibers.

15. The system of claim 11, wherein the layered structure is made of composite material.

16. The system of claim 11, wherein the layered structure comprises a laminate.

17. The system of claim 11, wherein the array of optical fibers comprises an array of substantially parallel optical fibers.

18. The system of claim 11, wherein the array of optical fibers comprises a grid of optical fibers.

* * * * *